(12) United States Patent
Coleman

(10) Patent No.: US 11,547,615 B2
(45) Date of Patent: Jan. 10, 2023

(54) DISPENSER FOR A STERILE BANDAGE ON A CONTINUOUS ROLL

(71) Applicant: Jeffrey Coleman, Delray Beach, FL (US)

(72) Inventor: Jeffrey Coleman, Delray Beach, FL (US)

(*) Notice: Subject to any disclaimer, the term of this patent is extended or adjusted under 35 U.S.C. 154(b) by 0 days.

(21) Appl. No.: 17/111,128

(22) Filed: Dec. 3, 2020

(65) Prior Publication Data

US 2021/0085539 A1  Mar. 25, 2021

Related U.S. Application Data

(63) Continuation of application No. 16/059,407, filed on Aug. 9, 2018, now abandoned.

(Continued)

(51) Int. Cl.
  *A61F 15/00*  (2006.01)
  *A61F 15/02*  (2006.01)
  *A61F 13/02*  (2006.01)

(52) U.S. Cl.
  CPC ........ *A61F 15/002* (2013.01); *A61F 13/0203* (2013.01); *A61F 13/0246* (2013.01); *A61F 15/02* (2013.01)

(58) Field of Classification Search
  CPC ................ A61F 15/002; A61F 13/0246; A61F 13/0203; A61F 15/02; A61F 13/0269;

(Continued)

(56) References Cited

U.S. PATENT DOCUMENTS

| 2,823,969 | A | * | 2/1958 | Traver | ............... | B65H 35/0086 |
| | | | | | | 83/454 |
| 3,142,217 | A | * | 7/1964 | Busse | ................ | B65H 35/0086 |
| | | | | | | 83/649 |

(Continued)

FOREIGN PATENT DOCUMENTS

WO    1997/017045 A1    5/1997

OTHER PUBLICATIONS www.ebay.co.uk/itm/Non-Irritating-First-Aid-Tape-Medical-Bandage-Strapping-Dispenser-Cut-To-Size-/311612798055 (Accessed Jul. 31, 2018).

(Continued)

*Primary Examiner* — Rakesh Kumar
(74) *Attorney, Agent, or Firm* — The Dobrusin Law Firm, P.C.; Bryan S. Lemanski

(57) ABSTRACT

A bandage configured to be administered from a continuous roll, comprising: (I) a first layer of flexible webbed material, the first layer including a self-adhesive disposed on a top surface; and (II) a second layer of flexible padded material adhered to the first layer along a longitudinal axis by the self-adhesive, the second layer having a width less than a width of the first layer so that a portion of the self-adhesive is exposed on each longitudinal side of the second layer; wherein the self-adhesive may releasably adhere to a bottom surface of the first layer in a rolled form so that, when unrolled, an adhesive bond is broken free of damaging the first layer; and wherein, when the self-adhesive is bonded to itself and opposing adhesive portions, the resulting peel strength is greater than a peel strength when the self-adhesive is bonded to skin.

18 Claims, 2 Drawing Sheets

Related U.S. Application Data

(60) Provisional application No. 62/543,000, filed on Aug. 9, 2017.

(58) Field of Classification Search
CPC ................ A61F 13/0236; A61F 13/023; A61F 13/0206; A61F 2210/0004; A61F 15/001; A61F 13/00072; A61F 13/551; A61F 15/00
USPC .............................................. 602/57; 221/70
See application file for complete search history.

(56) References Cited

U.S. PATENT DOCUMENTS

| | | | |
|---|---|---|---|
| 3,835,992 A * | 9/1974 | Adams, IV | B65D 83/0835 206/390 |
| 4,458,570 A * | 7/1984 | Morrison | B65H 35/002 220/524 |
| 4,853,074 A | 8/1989 | Manusch et al. | |
| 5,005,730 A | 4/1991 | Pickrell, Jr. et al. | |
| 5,133,477 A * | 7/1992 | Etheredge, III | B65D 75/366 206/460 |
| 5,782,786 A * | 7/1998 | Tomaiuolo | A61F 13/0203 602/41 |
| 5,843,011 A * | 12/1998 | Lucas | A61F 13/023 602/56 |
| 5,938,070 A | 8/1999 | Welborn et al. | |
| 6,155,454 A * | 12/2000 | George | A61J 7/0076 221/25 |
| 6,213,343 B1 | 4/2001 | Damikolas | |
| 6,362,388 B1 * | 3/2002 | Lucas | A61F 13/0203 602/56 |
| 6,756,519 B2 * | 6/2004 | Johnson | A61F 15/002 206/401 |
| 6,967,261 B1 * | 11/2005 | Soerens | A61L 15/46 602/41 |
| 7,012,170 B1 * | 3/2006 | Tomaiuolo | A61F 13/0203 602/41 |
| 7,077,289 B2 | 7/2006 | Ross | |
| 7,683,235 B2 | 3/2010 | Wendorf | |
| D633,213 S * | 2/2011 | Cowles | D24/189 |
| D637,299 S * | 5/2011 | Cowles | D24/189 |
| 8,020,703 B2 * | 9/2011 | List | A61B 50/3001 206/370 |
| 8,052,009 B2 | 11/2011 | Blum et al. | |
| 8,100,290 B2 | 1/2012 | Bizzell et al. | |
| 8,851,284 B2 | 10/2014 | Arefieg | |
| 9,492,260 B2 | 11/2016 | St. Anne | |
| 9,655,622 B2 * | 5/2017 | Jonn | A61F 13/0203 |
| 9,980,862 B2 | 5/2018 | Arefieg | |
| 10,016,310 B2 | 7/2018 | Caneppele | |
| 10,092,455 B2 * | 10/2018 | Eaves, III | A61F 13/00085 |
| 2003/0071051 A1 * | 4/2003 | Martinsen | G07F 11/68 156/767 |
| 2003/0225354 A1 * | 12/2003 | Drake | A61K 9/7084 428/40.1 |
| 2006/0161088 A1 * | 7/2006 | Voetsch | A61F 15/002 602/41 |
| 2007/0179466 A1 | 8/2007 | Tremblay et al. | |
| 2008/0135159 A1 | 6/2008 | Bries | |
| 2011/0160686 A1 * | 6/2011 | Ueda | A61F 13/0203 156/60 |
| 2012/0317820 A1 * | 12/2012 | McGushion | B26B 29/02 30/164 |
| 2013/0233876 A1 * | 9/2013 | Teates | A61F 15/002 221/70 |
| 2014/0012175 A1 * | 1/2014 | Oka | A61F 13/0206 602/58 |
| 2015/0238376 A1 | 8/2015 | Seibold | |
| 2019/0046370 A1 * | 2/2019 | Coleman | A61F 13/0246 |
| 2020/0085993 A1 * | 3/2020 | Karthikeyan | A61F 13/00068 |
| 2020/0188183 A1 * | 6/2020 | Hamerslagh | A61L 15/44 |

OTHER PUBLICATIONS www.sciencealert.com/10-year-old-cancer-survivor-is-heading-to-nasa-after-inventing-a-new-bandage-dispenser (Accessed Aug. 7, 2018).

* cited by examiner

DISPENSER FOR A STERILE BANDAGE ON A CONTINUOUS ROLL

FIELD

The present teachings generally relate to a bandage configured to bind a wound or to protect an injured appendage of the body. More specifically, the present teachings generally relate to dispenser for a bandage manufactured on a continuous roll, allowing a user to cut a desired length of bandage based on a specific wound size. The bandage roll may include a self-adhesive that removably adheres to a portion of the bandage yet can be overlapped to form a sufficient bond to protect a wounded appendage.

BACKGROUND OF THE INVENTION

Conventional self-adhesive bandages are typically packaged individually in a wrapper to avoid contamination of the bandage prior to application. The individual bandages are pre-cut to specific lengths, requiring a user to search for an appropriately sized bandage for a wound. Continuous rolls for self-adhesive bandages have been proposed to improve the convenience and customization of the bandages for users addressing wounds. However, continuous rolls often require special medical cutting tools (i.e., medical scissors) to cut a desired length of the bandage. Furthermore, continuous rolls are often difficult to cut, difficult to unroll manually, or both.

Additionally, a release paper adhered to the self-adhesive side of the bandage is often required so that the bandage can be rolled on itself without being contaminated. Further, without a release paper the bandage will adhere to itself, resulting in damage that renders the bandage unusable. Thus, a user is required to unroll a desired portion of the bandage, cut a desired length, and remove the release paper prior to application. Typically, a user will have difficulty removing the release paper without damaging the bandage piece or accidently adhering the bandage piece to itself.

Examples of such rolls may be found in the following potentially related documents: Published U.S. Patent Application 2007/0179466; U.S. Pat. Nos. 5,843,011; 6,362,388; 6,756,519; 8,851,284; and PCT Publication No. WO 97/17045, all of which are incorporated by reference herein for all purposes. It would be attractive to have a continuous bandage roll that is free of a release paper. What is needed is a bandage roll that may adhere to a portion of itself without damaging the bandage. It would be attractive to have a continuous bandage roll that easily unrolls and is cut to a desired length without damaging the bandage. What is needed is a bandage roll dispenser that is configured to unroll the bandage and cut the bandage to a desired length. It would be attractive to have a continuous bandage roll dispenser that protects the continuous bandage roll after cutting a portion of the bandage roll. What is needed is a bandage roll dispenser that secures a continuous bandage roll within the dispenser and remains enclosed while not in use. It would be attractive to have an alternative bandage roll assembly, particularly those in which the bandage can removably adhere to a portion of itself without damage, yet still have sufficient peel strength to remain in place when applied to a wound. What is needed is a continuous bandage roll configured to removably adhere to itself without damage, yet also remain in place when applied to a wound. It would be attractive to have a more advantageous bandage dispenser to meet one or more of the above needs.

SUMMARY

The present teachings meet one or more of the present needs by providing a bandage configured to be administered from a continuous roll, comprising: (I) a first layer of flexible webbed material, the first layer including a self-adhesive disposed on a top surface; and (II) a second layer of flexible padded material adhered to the first layer along a longitudinal axis by the self-adhesive, the second layer having a width less than a width of the first layer so that a portion of the self-adhesive is exposed on each longitudinal side of the second layer; wherein the self-adhesive may releasably adhere to a bottom surface of the first layer in a rolled form so that, when unrolled, an adhesive bond is broken free of damaging the first layer; and wherein, when the self-adhesive is bonded to itself and opposing adhesive portions, the resulting peel strength is greater than a peel strength when the self-adhesive is bonded to skin.

The present teachings meet one or more of the present needs by providing a bandage dispenser assembly comprising: (a) a dispenser having a body portion and a moveable portion, the moveable portion pivotally engaged to the body portion; and (b) a bandage according to claim 1 rotationally secured to a spindle mounted in a cavity of the dispenser, wherein a cutter is secured to the moveable portion so that, when a portion of the bandage is extending through an opening between the body portion and the moveable portion, the moveable portion pivots and cuts the bandage with the cutter.

The present teachings meet one or more of the present needs by providing a method of apply a bandage segment comprising: (I) unrolling a desired length of the bandage roll secured in the dispenser of claim 10; (II) cutting the bandage at the desired length with the blade to form a bandage segment; and (III) applying the bandage segment to a wound by adhering the first layer of the bandage segment to an area surrounding the wound so that the second layer is placed directly on the wound, wherein the first layer is free of contact with the wound.

The present teachings meet one or more of the present needs by providing a method of apply a bandage segment comprising: (I) unrolling a desired length of the bandage roll secured in the dispenser of claim 10; (II) cutting the bandage at the desired length with the blade to form a bandage segment; (Ill) placing a first portion of the bandage segment on a wound of an appendage so that the second layer of the bandage segment contacts the wound; (IV) folding a second portion of the bandage segment around or over the appendage; and (V) adhering the top surface of the first portion to the top surface of the second portion in a folded state, wherein the first layer is free of contact with the wound.

The present teachings meet one or more of the present needs by providing a continuous bandage roll, wherein: the first layer, the second layer, or both, are moisture-wicking; the first layer, the second layer, or both, are moisture absorbing; the second layer has a thickness of less than 1 cm; the second layer has a thickness of greater than 1 mm; the second layer has a thickness of less than 5 mm; the second layer is a gauze, plastic film, gel, foam, hydrocolloid, alginate, hydrogel, polysaccharide paste, or a combination thereof; the second layer includes one or more plies; the second layer is a single ply; one or more reagents are dispersed on the second layer; the one or more reagents is a medicament; the medicament is an antibiotic, anti-inflammatory, coagulator, disinfectant, scabicide, antifungal, or a combination thereof; the one or more reagents is a liquid, solid, gel, or a combination thereof; the one or more reagents include a release coating to promote long-term release of the one or more reagents; wherein the width of the second layer is less than 40% the width of the first layer; wherein the width of the second layer is approximately 40% to 90% the width of the first layer; the second layer is centered along the longitudinal axis of the first layer; the second layer is offset from the longitudinal axis of the first layer; the self-adhesive applied to the first layer has a uniform thickness, a varied thickness, or both; the self-adhesive is applied to the first layer in a continuous and uniform pattern as a plurality of dots, stripes, intermittent or disconnected patterns, or a combination thereof; or a combination thereof.

The present teachings meet one or more of the present needs by providing a continuous bandage roll, wherein the continuous bandage roll: is free of a release paper; may adhere to a portion of itself without damaging the bandage; easily unrolls and is cut to a desired length without damaging the bandage; can removably adhere to a portion of itself without damage, yet still have sufficient peel strength to remain in place when applied to a wound; or a combination thereof. The present teaching meet one or more of the present needs by providing a continuous bandage roll dispenser, wherein the dispenser: is configured to unroll the bandage and cut the bandage to a desired length; protects the continuous bandage roll after cutting a portion of the bandage roll; secures a continuous bandage roll within the dispenser and remains enclosed while not in use; or a combination thereof. The present teachings provide a more advantageous bandage dispenser to meet one or more of the present needs.

DETAILED DESCRIPTION

Figure 1:
FIG. 1 is a top view of a portion of a continuous bandage roll.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the description herein, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The teachings herein relate to a bandage dispenser assembly. The bandage dispenser assembly may function to dispense a continuous bandage roll, cut a portion of the continuous bandage roll, or both. The bandage dispenser assembly may function to provide a user a desired length of a bandage to apply to one or more wounds. The bandage dispenser assembly may comprise a dispenser, a continuous bandage roll, or both. The continuous bandage roll may be replaceable and/or removable from the dispenser so that the continuous bandage roll may be replaced. The bandage dispenser assembly may be configured for use one or more industries, such as the professional medical industry, consumer first aid care, home medical industry, industrial and/or commercial manufacturing, construction, or a combination thereof. The bandage dispenser assembly may be sufficiently portably so that the bandage dispenser assembly may be transferred from one location to another for different applications. The bandage dispenser assembly may vary in size and shape. For example, the bandage dispenser assembly may be sufficiently small to fit in a conventional backpack, purse, suitcase, satchel, or a combination thereof. Alternatively, the bandage dispenser assembly may be relatively large enough to mount on one or more surfaces. The bandage dispenser assembly may be customizable based on a consumer. For example, the bandage dispenser assembly may be marked with one or more identifiers for a hospital to indicate ownership, instructions for use, or both. The bandage dispenser assembly may include one or more automated components, one or more stationary components, one or more manually articulated components, or a combination thereof.

The bandage dispenser assembly may include a dispenser. The dispenser may function to dispense a portion of a continuous bandage roll so that a user may cut a desired length of the bandage roll. The dispenser may function to cut the bandage roll to a desired length. The dispenser may function to house a continuous bandage roll to protect the bandage roll from debris, damage, drying out, or a combination thereof. The dispenser may be any size and shape to house the bandage roll. The dispenser may include one or more openings, one or more covers, one or more housings, or a combination thereof. The dispenser may include one or more mounting features to mount the dispenser to one or more surfaces. For example, the dispenser may include one or more holes to receive one or more fasteners that secure the dispenser to a tabletop. The dispenser may free of mounting features. For example, the dispenser may be weighted so that the dispenser remains stationary during operation. The dispenser may include a plurality of components. The plurality of components may be integrally formed or secured to one another. The dispenser may be any material that may be formed into a desired shape of the dispenser. The dispenser may be metal, plastic, or both. The dispenser may be structurally rigid. The dispenser may include one or more compressible pieces. The dispenser may include one or more transparent components. For example, a body portion of the dispenser may be transparent so that a user may determine an amount of a bandage roll remaining in the dispenser without opening the dispenser. Alternatively, the dispenser may include one or more slots, cutouts, viewing windows, transparent panes, or a combination thereof to view the interior contents of the dispenser.

The dispenser may include a body portion. The body portion may function to secure the continuous bandage roll. The body portion may function to support the bandage roll during a cutting operation. The body portion may remain stationary during cutting of the bandage. The body portion may be any size and shape to securely house the bandage roll, yet allow unrolling of the bandage roll, rolling of the bandage roll, or both. The body portion may include a cavity to receive the bandage roll. The cavity may be encompassed by one or more walls that protect that cavity. The one or more walls may include one or more bends, angles, contours, projections, supporting members, or a combination thereof. The walls may vary in thickness. For example, the walls may have a thickness of about 5 mm or more, about 10 mm or more, or about 15 mm or more. The walls may have a thickness of about 30 mm or less, about 25 mm or less, or about 20 mm or less. The body portion may be one or more portions that abut a moveable portion of the dispenser. For example, the body portion may have a top surface having one or more contours that mate with one or more contours of a moveable portion of the dispenser when the dispenser is in a closed position, a cutting position, or both. The body portion may include one or more lips, one or more chamfered edges, one or more fillets, or a combination thereof. The body portion may be weighted. For example, the body portion may be substantially injection molded from a polyamide material and include an iron plate on a bottom surface to provide additional weight to the dispenser. The body portion may include one or more attachment points to secure a spindle, the bandage roll, or both. The attachment points may be connection means that movably secure the spindle, the bandage roll, or both so that the spindle, the bandage roll, or both may rotate. The attachment points may include one or more mechanisms to removably secure the spindle, the bandage roll, or both. For example, the one or more mechanisms may be a latch, hook, fastener, finger, lock, or a combination thereof.

The body portion may include one or more recesses. The one or more recesses may function to receive one or more features of the moveable portion of the dispenser. For example, the one or more recesses may receive a cutter of the dispenser, a nub of the dispenser, or both. The one or more recesses may be any size and shape to receive a size and shape of the cutter, the nub, or both. The one or more recesses may be positioned near a peripheral edge of the body portion. The one or more recesses may be positioned away from a peripheral edge of the body portion. A plurality of recesses may be positioned near each other. For example, a nub recess and a cutter recess may be adjacent to one another to receive a cutter and nub of the moveable portion of the dispenser that are adjacent to one another. The recesses may be integrally formed with the body portion. The recesses may be located on a portion of the dispenser other than the body portion. For example, the body portion may include a cutter that is received by a cutter recess of the moveable portion. The recesses may include one or more rounded surfaces, one or more flat surfaces, one or more bends, one or more contours, or a combination thereof. The recesses may include one or more friction modifiers, one or more teeth, one or more engaging features, or a combination thereof. For example, the cutter recess may include a magnetic surface to magnetically secure a metal cutter in the recess (i.e., to maintain a closed position of the dispenser whereby the moveable portion of the dispenser abuts the body portion of the dispenser to substantially encase a bandage roll. The recesses may include a substantially smooth surface. The recesses may be positioned near an opening of the dispenser (i.e., a portion of the dispenser where the bandage roll may be unrolled and extended beyond the confines of the dispenser). The recesses may receive the cutter of the dispenser, a nub of the dispenser, a projection of the dispenser, or a combination thereof while the body portion remains stationary and is support by one or more feet.

The feet may function to support the dispenser. The feet may function to maintain a position of the dispenser during use. The feet may be positioned anywhere along the dispenser to provide support. The feet may be integrally formed with the dispenser or may be attached by one or more fasteners, one or more adhesives, or a combination thereof. The feet may be adjustable. The feet may be movable. The feet may include one or more mounting features to mount the dispenser to one or more surfaces. The feet may be retractable. The feet may be structurally rigid or may be flexible. The feet may include one or more friction modifying surfaces. For example, the feet may include an abrasive surface that contacts one or more support surfaces to maintain a position of the dispenser and increase friction between the feet and the one or more support surfaces. The feet may maintain a position of the body portion during articulation of the moveable portion.

The moveable portion of the dispenser may function to articulate relative to the body portion to cut the bandage roll, enclose the bandage roll, or both. The moveable portion may be a shape substantially similar to the body portion. The moveable portion may be any size and shape that may mate to a size and shape of the body portion. The moveable portion may mate to the body portion in a closed position whereby the moveable portion and the body portion form a housing substantially enclosed. The moveable portion may articulate away from the body portion in an open position to allow the bandage roll to be unrolled and extend through the opening of the dispenser for cutting. The moveable portion may articulate away from the body portion to create an opening having a width large enough for a bandage roll to enter the dispenser, be removed from the dispenser, or both in a rolled state. The moveable portion may include one or more cavities, one or more contours, one or more flat portions, one or more angles, or a combination thereof. The moveable portion may include one or more cutters, one or more nubs, or both that contact the bandage roll, the body portion, or both during articulation. For example, a cutter may be positioned near a terminal edge of the moveable portion so that, when the moveable portion is moved in a cutting direction towards a recess of the body portion, the cutter contacts and cuts through the bandage prior to being received in the recess of the body portion. The moveable portion may articulate relative to the body portion via a pivot.

The pivot may function to allow articulation of the moveable portion relative to the body portion, or vice versa. The pivot may be any feature that allows movement of the moveable portion relative to the body portion. The pivot may be a joint, bearing, elastic member, biasing member, or a combination thereof. The pivot may be an elastic portion of the dispenser. For example, the body portion and the moveable portion may be integrally formed so that the pivot is an elastic portion of the dispenser that allows articulation of the moveable portion relative to the body portion. The pivot may be a notch, cutout, or both. The pivot may be located near a terminal edge of the body portion, the moveable portion, or both. The pivot may be a connection point between the body portion and the moveable portion. The pivot may allow for the moveable portion to articulate between an open position (i.e., a direction moving away from the body portion), a closed position (i.e., a position where the body portion and the moveable portion are in contact), one or more positions between the open position and the closed position, or a combination thereof. The pivot may allow the moveable portion to articulate approximately 30 degrees or more relative to the body portion, about 60 degrees or more relative to the body portion, or about 90 degrees or more relative to the body portion. The pivot may allow the moveable portion to articulate about 180 degrees or less relative to the body portion, about 150 degrees or less relative to the body portion, or about 120 degrees or less relative to the body portion. The pivot may allow the moveable portion to articulate so that a cutter of the moveable portion may contact a portion of a continuous bandage roll.

The cutter may function to cut a desired length of the bandage roll. The cutter may be positioned anywhere on the body portion, the moveable portion, or both. The cutter may be any cutting member that cuts a portion of the bandage without damaging the cut portion of the bandage roll, the remaining bandage roll, or both. The cutter may be mounted on the moveable portion of the dispenser to articulate in an opening direction (i.e., away from the body portion), a cutting direction (i.e., towards the body portion and the bandage roll), or a combination thereof. The cutter may be fixedly mounted to the moveable portion, the body portion, or both. The cutter may be moveable mounted to the moveable portion, the body portion, or both. For example, the cutter may be retractable in the moveable portion so that the cutter may be extended for cutting the bandage roll and then retracted after use to prevented accidental injury or damage. The cutter may be any size and shape to sufficiently cut through any bandage roll varying in size and shape. The cutter may include one or more lubricants to ensure that the cutter does not adhere to an adhesive layer of the bandage roll during cutting. The cutter may be received by one or more recesses of the dispenser in a closed position to prevent accidental injury. The cutter may be a blade, tooth, edge, any sharp portion of the dispenser, or a combination thereof. The cutter may be structurally rigid. The cutter may be removably attached to the dispenser to allow for replacement once the cutter has dulled. The cutter may be positionable along the dispenser to accommodate different bandage rolls. The cutter may be sufficiently sharp to cut through a bandage roll without bending or compressing the bandage roll. A plurality of cutters may be located on the dispenser. For example, a first blade may be located on the moveable portion and oppose a second blade located on the body portion so that, during cutting, the first blade and the second blade sandwich the bandage. Alternatively, a first and second blade may be located adjacent to one another on the moveable portion.

The cutter may be protected by a shield. The shield may function to cover the cutter and prevent unwanted contact between the cutter and a user. The shield may function to shield the cutter from a user, debris, moisture, or a combination thereof. The shield may be mounted near the cutter anywhere along the dispenser. The shield may be retractable. For example, the shield may move along a guide so that, when the moveable member is articulated in a cutting direction to contact the body portion, the shield moves in an opposing direction to prevent contact between the shield and the body portion. The shield may form a protective wall around all or a portion of the cutter. The shield may be structurally rigid or may be flexible. The shield may be integrally formed with the moveable portion, the body portion, or both.

The shield may be positioned near a nub of the dispenser. The nub may function to compress a portion of the bandage to enclose the bandage in the dispenser and prevent damage to the bandage, drying out of the bandage, or both. The nub may be positioned adjacent to the cutter. For example, the nub may contact the bandage during articulation of the moveable portion in a cutting direction so that the nub secures the bandage in position to allow the cutter to cut through the blade. The nub may help maintain a taught position of the bandage so that the cutter may cut through the bandage. The nub may be any size and shape to contact and secure the bandage without cutting through the bandage, damaging the bandage, or both. The nub may be received by a nub recess during closing of the dispenser, cutting of the bandage, or both. The nub may be integrally formed with the moveable portion, the body portion, or both. A plurality of nubs may be located on the dispenser. The nub may be a projection, contour, mound, step, or a combination thereof. The nub may have a shape that substantially mates with a nub recess of the dispenser. The nub may be replaceable. The nub may be positionable along the moveable portion, the body portion, or both. The nub may maintain a position of the bandage roll during a cutting operation after a portion of the bandage roll has been unrolled via a spindle. The nub may contact the bandage roll simultaneously with the cutter, prior to the cutter making contact with the bandage roll, after the cutter makes contact with the bandage roll, or a combination thereof.

The spindle may function to movably secure the bandage roll to the dispenser. The spindle may allow rotation of the bandage roll within the dispenser. The spindle may be any member that allows revolving of the bandage roll about an axis of the spindle. The bandage roll may revolve in a clockwise direction relative to the axis of the spindle, a counterclockwise direction relative to the axis of the spindle, or both. The spindle may be structurally rigid to support the bandage roll during rotation. The spindle may be removably attached to the moveable portion, the body portion, or both. The spindle may include one or more engaging features that engage the dispenser. For example, the spindle may include one or more fingers that engages one or more notches of the body portion. The spindle may be a rod, pin, tube, or a combination thereof. The spindle may have an outer diameter substantially equal to an inner diameter of the bandage roll so that the bandage roll remains in position once the spindle is secured to the bandage roll. The spindle may include one or more biasing members connecting one or more portions of the spindle. For example, the spindle may remain engaged to the body portion via a biasing member that expands opposing segments of the spindle. The biasing member may be compressed so that a length of the spindle temporarily decreases to allow the spindle to be removed form the dispenser to replace a bandage roll.

The bandage roll may function to provide a user a continuous bandage that may be cut into a desired length. The bandage roll may function to protect and/or cover a wound of a user. The bandage roll may be applied to any wounds of a user on any appendage. As such, the bandage roll may be sterile. The bandage roll may include one or more layers. The bandage roll may comprise a support layer, an absorbent layer, a release layer, an adhesive layer, or a combination thereof. The bandage roll when unrolled may be any desired length. The bandage roll may be any width. The bandage roll may be rolled and unrolled without damaging the bandage roll. The bandage roll may be configured to be enclosed within the dispenser. The bandage roll may include an inner tube that the bandage roll is rolled around. The bandage roll may be free of an inner tube. The bandage roll may include one or more perforations, one or more guidelines, or both to aid in cutting the bandage roll a desired length.

The bandage roll may include a support layer. The support layer may function to support one or more absorbent layers of the bandage. The support layer may function to adhere the bandage to one or more appendages, itself, or both. The support layer may be any flexible material. The support layer may be a webbed material, a woven material, an elastic material, or a combination thereof. The support layer may be fabric, plastic, or latex. The fabric may be woven or nonwoven. The plastic may be polyvinyl chloride, polyethylene, polyurethane, or a combination thereof. The support layer may be waterproof, moisture resistant, or both. The support layer may any size and shape. The support layer may be any desired thickness. For example, the support layer may have a thickness of about 0.5 mm or more, about 1 mm or more, or about 5 mm or more. The support layer may have a thickness of about 10 mm or less about 8 mm or less, or about 6 mm or less. The support layer may be perforated. The support layer may be a breathable material. The support layer may contain one or more antimicrobial reagents, antifungal reagents, or both.

The support layer may include one or more adhesives disposed on a surface of the support layer. The adhesive may be any contact adhesive sufficiently strong enough to adhere to a user's skin, itself, or both. The adhesive may be an acrylate, vinyl resin, or both. The adhesive may be disposed along an entire surface of the support layer or a portion of a surface of the support layer. For example, the adhesive layer may cover about 100% or less of the surface of the support layer, about 75% or less of the surface of the support layer, or about 50% or less of the surface of the support layer. The adhesive layer may cover about 10% or more of the surface of the support layer, about 25% or more of the surface of the support layer, or about 45% or more of the surface of the support layer. The adhesive layer may be applied uniformly in a continuous manner, in a patterned manner, or both. The pattern of the adhesive may be a plurality of dots, a plurality of strips, an intermittent or disconnected pattern, or a combination thereof. The adhesive layer may be applied in a nonuniform manner. The adhesive layer may have a uniform thickness. The adhesive layer may be configured for a desired peel strength. For example, the adhesive layer may have a peel strength that results in adhesive failure when contacting a user's skin, a portion of the bandage roll that is free of adhesive, or both, yet results in cohesive failure when the adhesive layer is applied to itself. As such, the adhesive layer may have a peel strength when bonded to itself that is greater than a peel strength when the adhesive layer is bonded to a user's skin, a portion of the bandage roll that is free of adhesive, or both. The peel strength of the support layer when the adhesive is adhered to itself may be about 50% or greater, about 75% or greater, or about 100% or greater when compared to a peel strength of the support layer when the adhesive is free of adhesion to itself. The peel strength of the support layer when the adhesive is adhered to itself may be about 200% or less, about 150% or less, or about 125% or less when compared to a peel strength of the support layer when the adhesive is free of adhesion to itself. The adhesive layer may allow for the bandage to be rolled on itself so that, when the bandage is unrolled, the bandage is free of damage or cohesive failure. The adhesive layer may be free of contact with one or more wounds when the bandage is applied to the one or more wounds. The adhesive layer may be configured to adhere an absorbent layer to the support layer.

The absorbent layer may function to directly contact one or more wounds of a user. The absorbent layer may function to protect the one or more wounds. The absorbent layer may be any sterile material that protects the one or more wounds from moisture, bacteria, or both. The absorbent layer may be a fabric, polymer, or both. The fabric may be woven or nonwoven. The fabric may cotton, wool, other fibrous material, or a combination thereof. The absorbent layer may be a gauze, plastic film, gel, foam, hydrocolloid, alginate, hydrogel, polysaccharide paste, or a combination thereof. The absorbent layer may include one or more coatings on a surface layer to prevent the absorbent layer from sticking to the one or more wounds. The one or more coatings may be a polymer coating. The absorbent layer may be a plurality of layers. For example, the absorbent layer may include a plurality of plies. The absorbent layer may be compressible. The absorbent layer may be nonabrasive. The absorbent layer may include one or more padding materials. The absorbent layer may be moisture wicking, moisture resistant, or both. A surface of the absorbent layer may be flush with the surface of the support layer having the adhesive layer. For example, the support layer may include a recessed portion that extends longitudinally along the support layer that receives the absorbent layer so that the surface of the support layer and the surface of the absorbent layer are coplanar.

The absorbent layer may include one or more reagents dispersed on a surface of the absorbent layer. The one or more reagents may be a medicament, antibiotic, anti-inflammatory, coagulator, disinfectant, scabicide, antifungal, or a combination thereof. The one or more reagents may be a liquid, a sold, a gel, or a combination thereof. The one or more reagents may include a release coating to promote long-term release of the one or more reagents.

The absorbent layer may be any size and shape to adhere to the support layer. The absorbent layer may have a width less than a width of the support layer so that the absorbent layer is fully supported and contained on a surface of the support layer. The absorbent layer may be sufficiently adhered to the support layer to prevent separation between the absorbent layer and the support layer. The absorbent layer may be positioned substantially along a longitudinal axis of the support layer. The absorbent layer may be positioned off centered from the longitudinal axis of the support layer. The absorbent layer may have a width less than the support layer. For example, the width of the absorbent layer may be about 100% or less, about 75% or less, or about 50% or less than a width of the support layer. The width of the absorbent layer may be about 10% or more, about 25% or more, or about 45% or more than a width of the support layer. The absorbent layer may vary in thickness. The absorbent layer may have a thickness of about 0.5 mm or more, about 1 mm or more, or about 5 mm or more. The absorbent layer may have a thickness of about 10 mm or less, about 8 mm or less, or about 6 mm or less.

The absorbent layer, the support layer, or both may be protected by a release material layer. The release material layer may function to cover the absorbent layer, the support layer, or both prior to application of the bandage roll to one or more wounds. The release material layer may be configured to release from the adhesive of the support layer without damaging the bandage roll. The release material layer may be removed prior to cutting the bandage, after cutting the bandage, or both. The release material layer may be any material, such as paper, plastic, or both. The release material layer may include one or more coating to decrease adherence between the release material layer and the support layer, the absorbent layer, or both. The release material layer may include one or more perforation, one or more lines, or both to aid in cutting the bandage roll to a desired length. The release material layer may allow a user to extend a portion of the bandage roll beneath the cutter to a desired length and maintain a force on the bandage roll to keep the bandage taught during cutting.

Turning now to the figures, FIG. 1 illustrates a top view of a portion of a continuous bandage roll 12. The bandage roll 12 includes a support layer 14 having an adhesive disposed on a surface of the support layer 14. An absorbent layer 16 is disposed along a portion of the surface of the support layer 14 having the adhesive. As shown, the absorbent layer 16 has a width ($W_A$) that is less than a width of the support layer 14 ($W_S$) so that a portion of the support layer 14 is exposed on opposing sides of the absorbent layer 16. It should be noted that the absorbent layer 16 may be disposed on the support layer 14 at any position.

Figure 2:
FIG. 2 is a side view of a portion of a continuous bandage roll.

FIG. 2 illustrates a side view of a portion of a continuous bandage roll 12. The bandage roll 12 includes a support layer 14 having an adhesive disposed on a surface of the support layer 14. An absorbent layer 16 is disposed along a portion of the surface of the support layer 14 having the adhesive. A release material layer 18 is disposed on the continuous bandage roll 12 to protect the support layer 14 and the absorbent layer 16 prior to application.

Figure 3:
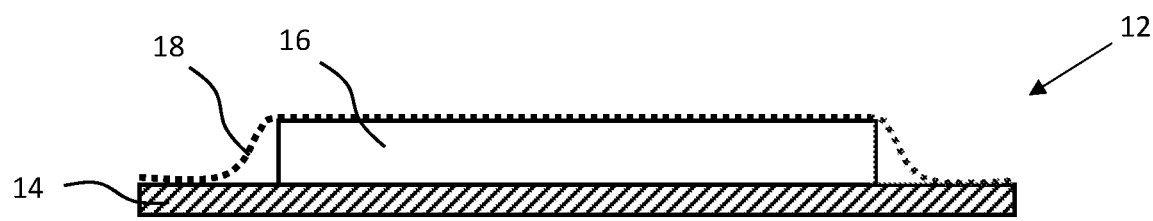
FIG. 3 is a front view of a portion of a continuous bandage roll.

FIG. 3 illustrates a front view of a portion of a continuous bandage roll 12. The bandage roll 12 includes a support layer 14 having an adhesive disposed on a surface of the support layer 14. An absorbent layer 16 is disposed along a portion of the surface of the support layer 14 having the adhesive. A release material layer 18 is disposed on the continuous bandage roll 12 to protect the support layer 14 and the absorbent layer 16 prior to application. As shown, the release material layer 18 is disposed to cover substantially a width of the support layer 14 and a width of the absorbent layer 16.

Figure 4:
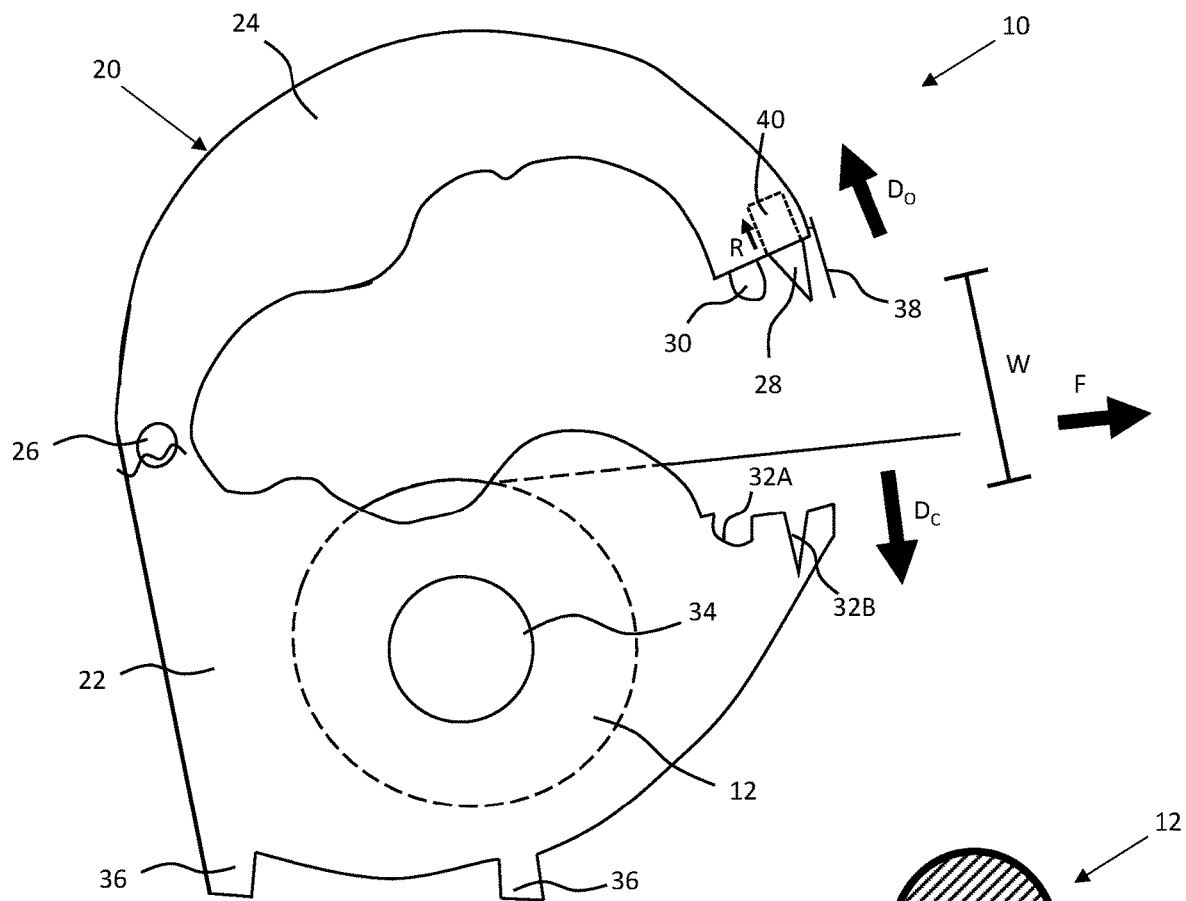
FIG. 4 is a side view of a bandage dispenser assembly.

FIG. 4 illustrates a side view of a bandage dispenser assembly 10. The bandage dispenser assembly 10 includes a dispenser 20 having a body portion 22 and a moveable portion 24. The moveable portion 24 is configured to move relative to the body portion 22 about a pivot 26 while the body portion 22 remains stationary and supported by a plurality of feet 36. A bandage roll 12 is movably secured to a spindle 34 of the dispenser 20 so that the bandage roll 12 may be unrolled to cut a desired length of the bandage 12. To cut a portion of the bandage roll 12, the moveable portion 24 is moved in an opening direction ($D_O$) to create a desired width (W) of an opening of the dispenser 20. Once the dispenser 20 is opened to a desired width (W), the bandage roll 12 is unrolled and extended beneath a nub 30 and a cutter 28 by applying a force (F) on the bandage roll 12. After the bandage roll 12 is unrolled and extended a desired length, the cutter 28 is moved in a cutting direction ($D_C$) until the cutter 28 is received by a cutter recess 32B, thereby cutting through the bandage roll 12. Additionally, the nub 30 compresses a portion of the bandage roll 12 into a nub recess 32A to protect the remaining portion of the bandage roll 12 enclosed in the dispenser 20, thereby preventing exposure to debris or damage, preventing the bandage from drying out, or both. It should be noted that the nub 30 may compress the bandage roll 12 prior to cutting to ensure the bandage roll 12 remains intact and free from debris or damage. A retractable shield 38 surrounding at least a portion of the cutter 28 protects a user from accidental injury by contacting the cutter 28. The retractable shield 38 may retract in an opposing direction to the cutting direction ($D_C$) to prevent contact between the retractable shield 38 and the body portion 22. Additionally, it should be noted that the cutter 28 may be retracted into confines 40 of the moveable portion 24 when not in use in a retraction direction (R).

Figure 5:
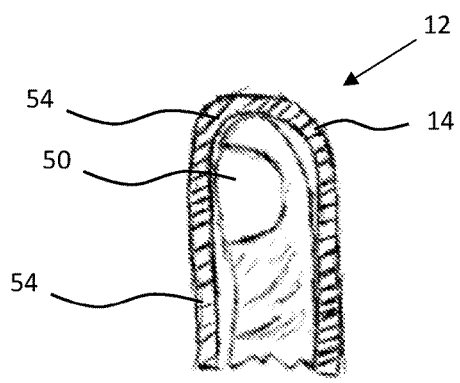
FIG. 5 is a perspective view of a cut portion of a bandage roll applied to an appendage prior to fully adhering the bandage.

FIG. 5 illustrates a perspective view of a cut portion of a bandage roll 12 applied to an appendage 50 prior to fully adhering the bandage roll 12. As shown, a portion of the bandage roll 12 is cut in accordance with the present teachings (see FIG. 4) to a desired length along one or more perforations 54 of a support layer 14 of the bandage roll 12 to protect the appendage 50. Once cut, the bandage 12 is applied around the appendage 50 so that a surface of the support layer 14 of the bandage 12 is joined to itself and/or the appendage 50, ensuring the appendage 50 remains protected and the bandage 12 remains in position (see FIG. 6).

Figure 6:
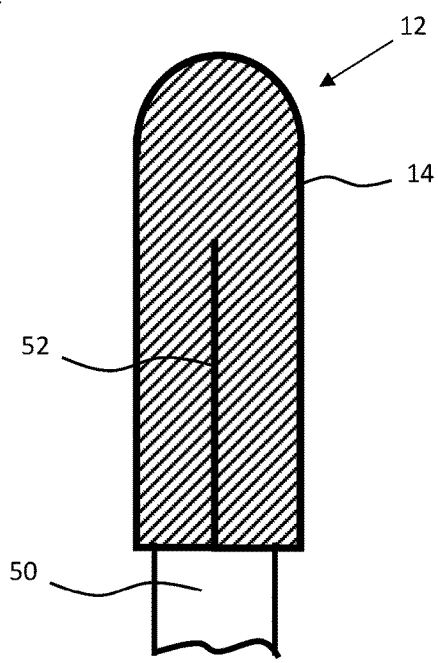
FIG. 6 is a perspective view of the cut portion of the bandage roll of FIG. 5 after fully adhering the bandage.

FIG. 6 illustrates a perspective view of the cut portion of the bandage roll 12 of FIG. 5. As shown, the support layer 14 of the bandage 12 is applied over the appendage 50 so an adhesive surface of the support layer 14 adheres to itself to form an adhered portion 52 and encompass the appendage 50 (see FIG. 1).

The explanations and illustrations presented herein are intended to acquaint others skilled in the art with the invention, its principles, and its practical application. The above description is intended to be illustrative and not restrictive. Those skilled in the art may adapt and apply the invention in its numerous forms, as may be best suited to the requirements of a particular use.

Accordingly, the specific embodiments of the present invention as set forth are not intended as being exhaustive or limiting of the teachings. The scope of the teachings should, therefore, be determined not with reference to this description, but should instead be determined with reference to the appended claims, along with the full scope of equivalents to which such claims are entitled. The omission in the following claims of any aspect of subject matter that is disclosed herein is not a disclaimer of such subject matter, nor should it be regarded that the inventors did not consider such subject matter to be part of the disclosed inventive subject matter.

Plural elements or steps can be provided by a single integrated element or step. Alternatively, a single element or step might be divided into separate plural elements or steps.

The disclosure of "a" or "one" to describe an element or step is not intended to foreclose additional elements or steps.

While the terms first, second, third, etc., may be used herein to describe various elements, components, regions, layers and/or sections, these elements, components, regions, layers and/or sections should not be limited by these terms. These terms may be used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The disclosures of all articles and references, including patent applications and publications, are incorporated by reference for all purposes. Other combinations are also possible as will be gleaned from the following claims, which are also hereby incorporated by reference into this written description.

Unless otherwise stated, a teaching with the term "about" or "approximately" in combination with a numerical amount encompasses a teaching of the recited amount, as well as approximations of that recited amount. By way of example, a teaching of "about 100" encompasses a teaching of within a range of 100+/−15.

ELEMENT LIST

10 Bandage Dispenser Assembly
12 Bandage Roll
14 Support Layer
16 Absorbent Layer
18 Release Material Layer
20 Dispenser
22 Body Portion
24 Moveable Portion
26 Pivot
28 Cutter
30 Nub
32 Recess
32A Nub Recess
32B Cutter Recess
34 Spindle
36 Foot
38 Shield
40 Confines
50 Appendage
52 Adhered Portion
54 Perforation
W Width of Opening of Dispenser
F Force on Bandage
$D_O$ Direction of Opening of Dispenser
$D_C$ Cutting Direction
R Retraction Direction

The invention claimed is:

1. A bandage dispenser comprising:
(I) a body portion;
(II) a moveable portion pivotally engaged to the body portion;
(III) a cutter extending from the moveable portion, wherein the cutter is configured to cut a bandage extending through an opening between the body portion and the moveable portion and the cutter is received by a cutter recess that is located in the body portion during cutting of the bandage; and
(IV) a nub extending from the moveable portion and positioned adjacent to the cutter, wherein the nub is configured to compress a portion of the bandage in a nub recess and substantially enclose a remaining uncut portion of the bandage within a cavity of the bandage dispenser,
wherein the bandage dispenser includes a shield extending from an exterior surface of the moveable portion substantially parallel to the cutter to protect a user from contacting the cutter during use of the dispenser,
wherein the shield is retractable so that, when the moveable member is moved towards the body portion to contact the body portion, the shield moves in an opposing direction to prevent contact between the shield and the body portion.

2. The bandage dispenser according to claim 1, wherein the cutter recess is complimentary in shape to the cutter in a nesting relation.

3. The bandage dispenser according to claim 2, wherein the nub is complimentary in shape to the nub recess in a nesting relation.

4. The bandage dispenser according to claim 3 wherein a force is applied to the bandage to extend the bandage through the opening and maintain a taught position of the bandage for cutting.

5. The bandage dispenser according to claim 4, wherein the nub is positioned closer to an interior of the bandage dispenser relative to the cutter.

6. The bandage dispenser according to claim 5, wherein the nub compresses the portion of the bandage during cutting of the bandage.

7. The bandage dispenser according to claim 5, wherein the nub contacts the portion of the bandage after the cutter contacts the bandage.

8. The bandage dispenser according to claim 1, wherein the cutter retracts within confines of the moveable portion when not in use for cutting the bandage.

9. The bandage dispenser according to claim 8, wherein the moveable portion and the body portion are integrally formed together and the moveable portion rotates about a pivot of the bandage dispenser.

10. The bandage dispenser according to claim 9, wherein the pivot is an elastic portion of the dispenser connecting the moveable portion and the body portion.

11. The bandage dispenser according to claim 9, wherein the pivot is a notch or cutout of the dispenser and the moveable portion articulates 60 degrees or more relative to the body portion.

12. The bandage dispenser according to claim 3, wherein the nub recess is located in the body portion adjacent to the cutter recess.

13. The bandage dispenser according to claim 12, wherein the bandage is a bandage roll located within the cavity of the dispenser, and the bandage roll is at least partially unrolled to extend through the opening between the body portion and the moveable portion.

14. The bandage dispenser according to claim 13, further comprising a spindle positioned within the cavity of the bandage dispenser that movably secures the bandage roll.

15. The bandage dispenser according to claim 14, wherein the spindle is removably secured to the body portion.

16. The bandage dispenser according to claim 15, further comprising feet projecting from the body portion to support the bandage dispenser during operation.

17. The bandage dispenser according to claim 13, wherein the bandage comprises:
(a) a waterproof support layer of flexible webbed material, the support layer including a self-adhesive disposed on a top surface, the self-adhesive covering about 100% of the top surface;
(b) an absorbent layer of flexible padded material adhered to the support layer along a longitudinal axis by the self-adhesive, the absorbent layer being moisture wicking and moisture resistant and having a width less than a width of the support layer so that a portion of the self-adhesive is exposed on each longitudinal side of the absorbent layer; and
(c) a release layer adhered to the top surface of the support layer and removed prior to applying the bandage to a desired area, wherein the release layer includes one or more coatings to decrease adherence between the release layer and the support layer, the absorbent layer, or both;
wherein the width of the absorbent layer is approximately 40% to 90% the width of the support layer.

18. The bandage dispenser according to claim 17, wherein the support layer has a thickness of less than 5 mm, the absorbent layer includes one or more antimicrobial reagents, antifungal reagents, or both dispersed on a surface layer of the absorbent layer, and the absorbent layer is nonabrasive and includes a polymer coating on a surface to prevent the absorbent layer from sticking to the desired area.

* * * * *